US00PP10619P

United States Patent [19]

Pouw

[11] Patent Number: Plant 10,619

[45] Date of Patent: Sep. 29, 1998

[54] HYBRID TEA ROSE PLANT NAMED 'RUIKWIEN'

[75] Inventor: A. A. Pouw, Kwakel, Netherlands

[73] Assignee: De Ruiter's Nieuwe Rozen B.V., Kwakel, Netherlands

[21] Appl. No.: 759,607

[22] Filed: Dec. 5, 1996

[51] Int. Cl.[6] ..... A01H 5/00

[52] U.S. Cl. ..... Plt./11

[58] Field of Search ..... Plt./11, 16, 18

*Primary Examiner*—Howard J. Locker

*Attorney, Agent, or Firm*—Christie, Parker & Hale, LLP

[57] ABSTRACT

A new variety of hybrid tea rose plant producing light pink/orange blend flowers of good form and suitable for growing under glass.

1 Drawing Sheet

BACKGROUND OF THE INVENTION

The present invention relates to a new and distant variety of rose plant of the Hybrid Tea rose class which was created by crossing undistributed, unnamed and unpatented seedlings as seed and pollen parents in De Kwakel, Holland. The varietal denomination of the new variety is 'Ruikwien'. The new variety was isolated and asexually reproduced by budding in Holland.

SUMMARY OF THE INVENTION

Among the novel characteristics possessed by this new variety which distinguish it from its parents and all other varieties of which I am aware are its attractive light pink/orange blend flowers of good form borne on a floriferous plant with long stems and suitable for production of cut flowers under glass. The new variety can be reproduced through propagation by cuttings, grafting, budding and micropropagation.

Asexual reproduction by budding of the new variety as performed in Holland shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety in different stages of development depicted in color as nearly true as it is reasonably possible to make the same in a color illustration of this character.

DESCRIPTION OF THE NEW VARIETY

The following is a detailed description of the new variety, with color terminology in accordance with The Royal Horticultural Society Colour Chart (RHSCC) and horticultural terminology in 5 accordance with standard terminology used in UPOV-approved horticultural guideline. The terminology used in color descriptions herein refers to plate numbers in the aforementioned color chart. Phenotypic expression may vary depending upon growing conditions under different climate, soil, and cultivation conditions.

Parentage: Seed and pollen parents are seedlings.
Class: Hybrid Tea.

As can be seen in the accompanying detail illustration there is shown a new shoot and green bud, 1; compound three, five and seven leaflet leaves, 2, 3 and 4, respectively; a stem, 5; buds, 6 and 8; a flower, 7, about one-third open; and a flower, 9, more fully open. Also shown are flower stems 10, 11 and 12, with reproductive organs displayed.

The following further horticultural description is based on observations made of specimens grown under glass in Holland.

Flower

Blooming habit: Nearly continuous.

A. Bud:

(1) *Size.*—Medium, about 3 cm long and about 2 cm wide.

(2) *Form.*—Ovate (shape of longitudinal section just before separation of sepals); urn-shaped after sepals part.

(3) *Color.*—As sepals divide, near 29B with darker orange red edge.

(4) *Sepals.*—Much longer than green bud, generally foliated, lower surface coloration of sepals near 146C turning to purple to the top as of anthocyan; irregular coloring of anthocyan; uppersurface coloration of sepals near 146B.

(5) *Peduncle.*—Long: Strength-erect, very strong. Color-medium green, near 147B to 147C.

B. Bloom:

*Flower.*—Medium; viewed from above — irregularly rounded; viewed from side — (a) upper part of fully opened flower, flattened convex; (b) lower part of fully opened flower, flattened convex.

(1) *Size.*—Average size when fully expanded — about 7 cm.

(2) *Borne*—Singly, one to a stem.

(3) *Form.*—Pointed center, exhibition type, somewhat flat top, spiral imbricated, outer petals reflex to points.

(4) *Petalage.*—About 33; about 13 petaloids, crinkled and about 3×3 cm in size.

(5) *Color.*—After sepals part and petals unfurl color of middle zone of top surface appears near 13B; petal top surface (⅓ to full open) marginal zone near 55B to 55C; middle zone of underside near 55B, marginal zone near 55B. Zone of petal attachment near 13B to 13C. Pinkish margin color not seen on inner petals but is apparent on outer few rows of petals. Overall tonality from a distance is attractive light pink/orange blend.

(6) *Peduncle.*—Generally smooth.

(7) *Fragrance.*—Weak.

Petals:

(1) *Texture.*—Crisp.

(2) *Appearance.*—Inside velvety and outside satiny.

(3) *Form and size*—Broad, medium, little or no undulation of margin.

(4) *Arrangement.*—Regularly arranged, imbricated.

(5) *Petaloids.*—Around 13.

(6) *Lasting quality.*—Long-lasting quality on plant and after cutting. Vaselife is about 18 days; blooms on the plant can last more than 25 days because of persistence; at the end of the flowering period the bloom fades to greenish/grey and the petals last on the plant.

(7) *Production.*—About 300 flowering stems/$m^2$/year in Holland under glassy.

Reproductive Organs

A. Stamens, filaments and anthers:

*Arrangement and color.*—Regularly arranged around styles; color of filaments — yellow.

B. Pollen: Color — near 13A.

C. Styles: Long, stigma above mouth of receptacle, yellow.

D. Stigmas: Yellow, positioned below anthers.

E. Hip: Pitcher-shaped; small seed vessel at petal fall however, normally there is no seed set so hips become brown and die after flowering.

Plant

A. Form: Narrow, bushy, average disease resistance.

B. Growth: Vigorous up to about 1.5 m in height and about 0.5 m in width.

C. Foliage: Compound 3, 5 and 7 leaflets.

(1) *Size.*—Size of top of leaf about 7.75×8 to 9 cm; total foliage length about 17 to 19 cm.

(2) *Quantity.*—Abundant.

(3) *Color.*—Juvenile foliage — red purple to bronze-reddish brown; near 180A; medium to strong anthocyanin coloration, (shoot about 20 cm long); mature leaf color — near 136A, undersurface near 137B.

(4) *Shape.*—Broad oval.

(5) *Texture.*—Upper side is medium glossy; underside is matte.

(6) *Edge.*—Serrate.

(7) *Serration.*—Ordinary, acuminate apices.

(8) *Leaf stem.*—Color — medium green, near 147A to 147B.

(9) *Stipules.*—Short, simple, medium green, distinct auricle.

(10) *Leaflets.* Cross section slight concave: strong undulation of margin; terminal leaflet — medium length and width; blade about 4 to 6 cm long and 4 to 5 cm wide, rounded base.

D. Wood:

(1) *New wood.*—Color — 139B to 139C; young shoots have weak to medium anthocyanin; coloration — bronze red purple to reddish brown (2) *Old wood.*—Color — medium green, near 147A to 147B.

E. Prickles (thorns):

(1) *Prickles.*—Present; quantity (main stalk) — ordinary; Shape of lower side — concave; Length — short prickles absent or very few, long prickles average; Color — near 159A; Position — irregular.

F. Disease Resistance: Average resistance to powdery and downy mildew.

What is claimed is:

1. A new and distinct variety of rose plant of the hybrid tea rose class, substantially as shown and described.

* * * * *

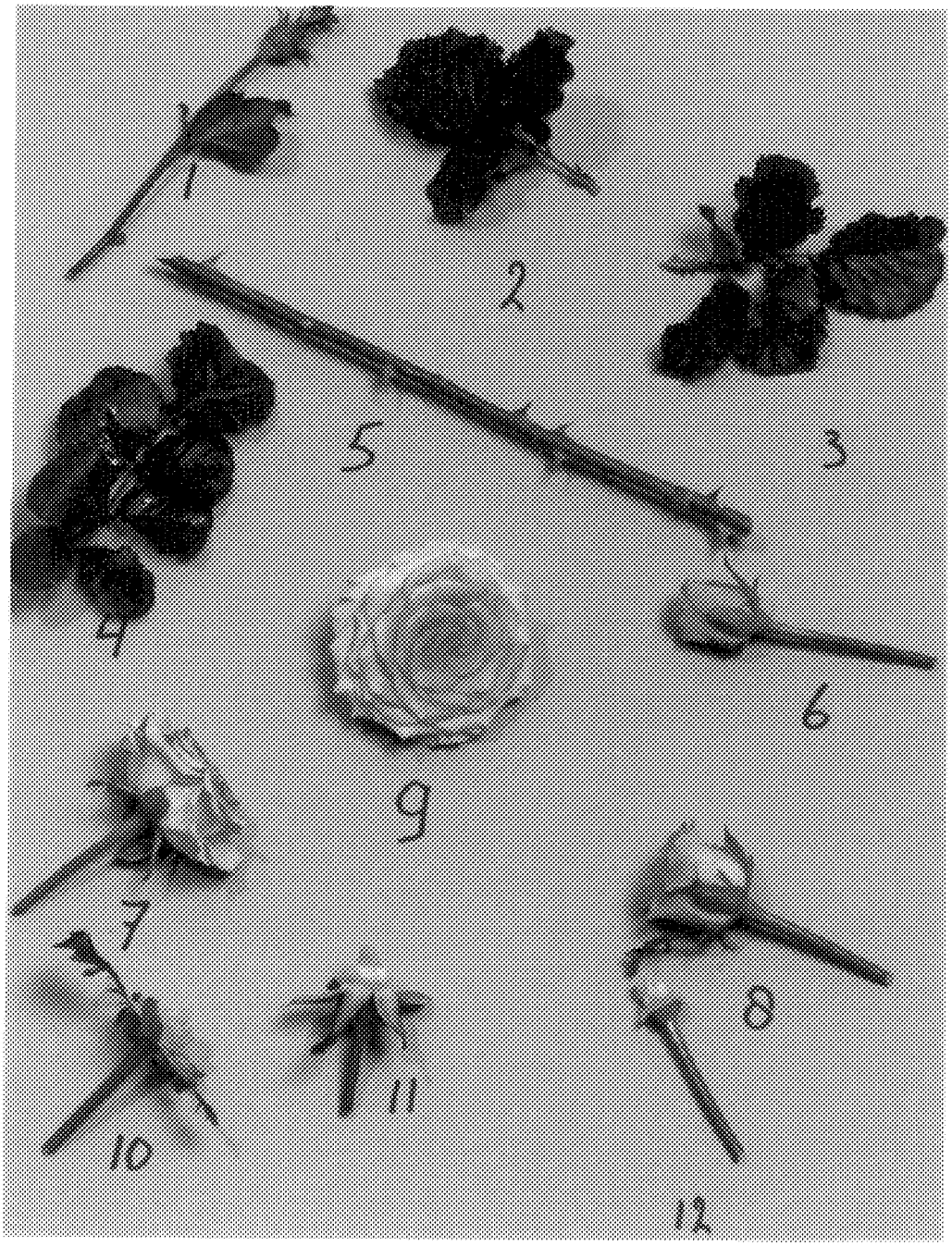
1
2
3
4
5
6
7
8
9
10
11
12